US 11,744,910 B1

(12) United States Patent
Buckner

(10) Patent No.: US 11,744,910 B1
(45) Date of Patent: Sep. 5, 2023

(54) DISINFECTION APPARATUS AND RELATED METHODS OF USE

(71) Applicant: Todd T. Buckner, Tifton, GA (US)

(72) Inventor: Todd T. Buckner, Tifton, GA (US)

( * ) Notice: Subject to any disclaimer, the term of this patent is extended or adjusted under 35 U.S.C. 154(b) by 274 days.

(21) Appl. No.: 17/116,518

(22) Filed: Dec. 9, 2020

Related U.S. Application Data

(60) Provisional application No. 63/014,826, filed on Apr. 24, 2020.

(51) Int. Cl.
| | |
|---|---|
| *A61L 2/22* | (2006.01) |
| *B65G 15/12* | (2006.01) |
| *B65G 47/24* | (2006.01) |
| *A61L 2/26* | (2006.01) |
| *B65G 47/66* | (2006.01) |
| *F26B 5/04* | (2006.01) |

(52) U.S. Cl.
CPC .............. *A61L 2/22* (2013.01); *A61L 2/26* (2013.01); *B65G 15/12* (2013.01); *B65G 47/24* (2013.01); *F26B 5/041* (2013.01); *A61L 2202/122* (2013.01); *A61L 2202/15* (2013.01); *A61L 2202/23* (2013.01); *B65G 47/66* (2013.01)

(58) Field of Classification Search
CPC ........ A61L 2/22; A61L 2/26; A61L 2202/122; A61L 2202/15; A61L 2202/23; B65G 15/12; B65G 47/24; B65G 47/66; F26B 5/041
See application file for complete search history.

(56) References Cited

U.S. PATENT DOCUMENTS 3,291,143 A * 12/1966 Huddle ............... B05B 13/0221
248/500
5,335,682 A * 8/1994 Yoshimura ............... B08B 3/022
134/131
(Continued)

FOREIGN PATENT DOCUMENTS

| CN | 103303529 B | * | 3/2016 |
| CN | 206464292 U | * | 9/2017 |

(Continued)

OTHER PUBLICATIONS

CN 109099698 Translation, 2018.
KR 200422498 Translation, 2006.

*Primary Examiner* — Jennifer Wecker
*Assistant Examiner* — Brady C Pilsbury
(74) *Attorney, Agent, or Firm* — Taylor English Duma

(57) ABSTRACT

A disinfection apparatus disclosed herein includes a chamber and a conveyor belt adapted to convey an object through the chamber, in various aspects. A nozzle array comprising at least one nozzle is positioned beneath the conveyor belt to spray a disinfectant through apertures formed in the conveyor belt onto a surface of the object oriented toward the conveyor belt, the spray communicated upward through apertures formed in the conveyor belt, in various aspects. A blower array comprising at least one blower nozzle is positioned beneath the conveyor belt to blow an air jet through apertures formed in the conveyor belt onto the surface of the object to dry the disinfectant from the object, the air jet communicated upward through apertures formed in the conveyor belt. Related methods of disinfecting objects are also disclosed herein.

3 Claims, 6 Drawing Sheets

(56) References Cited

U.S. PATENT DOCUMENTS

| | | | |
|---|---|---|---|
| 8,529,833 B2* | 9/2013 | Morgantini | B05B 5/0407 |
| | | | 239/700 |
| 2012/0107184 A1 | 5/2012 | Asiyanbola et al. | |
| 2018/0332882 A1* | 11/2018 | Wansitler | B08B 3/022 |

FOREIGN PATENT DOCUMENTS

| | | | |
|---|---|---|---|
| CN | 109099698 | | 12/2018 |
| CN | 110201198 A | * | 9/2019 |
| KR | 200422498 | | 7/2006 |

* cited by examiner

DISINFECTION APPARATUS AND RELATED METHODS OF USE

CROSS-REFERENCE TO RELATED APPLICATIONS

This application claims priority to and benefit of U.S. Provisional Patent Application No. 63/014,826, filed on Apr. 24, 2020, which is hereby incorporated by reference in its entirety herein.

FIELD OF THE INVENTION

This disclosure relates to disinfection, and, more particularly, to apparatus and related methods of use for disinfection of objects.

BACKGROUND OF THE INVENTION

There are many settings in which a number of objects are collected, distributed, or transported and distributed. For example, objects in the form of luggage may be collected at an airport terminal and then placed within an aircraft for transport. The luggage is then distributed from the aircraft at a destination of the aircraft. As another example, objects in the form of containers may be transported, distributed, or transported and then distributed from a warehouse. As yet another example, objects in the form of mail including postcards, envelopes, and packages may be collected, transported, and then distributed.

Objects, as used herein, may include people that may collect at or be distributed from, for example, industrial facilities, offices, retail stores, restaurants, transport facilities such as airports, bus terminals, train stations, entertainment venues such as theatres, stadiums, and arenas, and healthcare facilities such as hospitals, nursing homes, and clinics. Objects in the form of people may be transported, for example, by vehicle, light rail, rail, or aircraft between collection and distribution, in various aspects.

The COVID-19 epidemic provides a dramatic example of the need to provide mass disinfection to objects during collection, transport, and/or distribution in order to prevent spread of disease by collection, transport, and/or distribution of contaminated objects. Other diseases such as influenza may also be spread by collection, transport, and/or distribution of contaminated objects. Furthermore, it may be anticipated that other perhaps more virulent epidemics will occur in the future.

Accordingly, there is a need for improved apparatus as well as related methods for disinfection of objects during collection, transport, and/or distribution.

BRIEF SUMMARY OF THE INVENTION

These and other needs and disadvantages may be overcome by the apparatus and related methods disclosed herein. Additional improvements and advantages may be recognized by those of ordinary skill in the art upon study of the present disclosure.

A disinfection apparatus disclosed herein includes a chamber and a conveyor belt adapted to convey an object through the chamber, in various aspects. A nozzle array comprising at least one nozzle is positioned beneath the conveyor belt to spray a disinfectant through apertures formed in the conveyor belt onto a surface of the object oriented toward the conveyor belt, the spray communicated through apertures formed in the conveyor belt, in various aspects. A blower array comprising at least one blower nozzle is positioned beneath the conveyor belt to blow an air jet through apertures formed in the conveyor belt onto the surface of the object to dry the disinfectant from the object, the air jet communicated through apertures formed in the conveyor belt.

Related methods of disinfecting objects are disclosed herein. In various aspects, the methods include the step of conveying an object through a chamber using a plurality of conveyor belts mechanically cooperating with one another within the chamber and the step of transferring the object between conveyor belts of the plurality of conveyor belts thereby altering an alignment of a surface of the object oriented toward each conveyor belt with apertures formed in each conveyor belt of the plurality of conveyor belts. In various aspects, the methods include the step of spraying a disinfectant through apertures formed in each conveyor belt of the plurality of conveyor belts onto a portion of the surface of the object aligned with the apertures of each conveyor belt of the plurality of conveyor belts.

This summary is presented to provide a basic understanding of some aspects of the apparatus and methods disclosed herein as a prelude to the detailed description that follows below. Accordingly, this summary is not intended to identify key elements of the apparatus and methods disclosed herein or to delineate the scope thereof.

Figure 1:
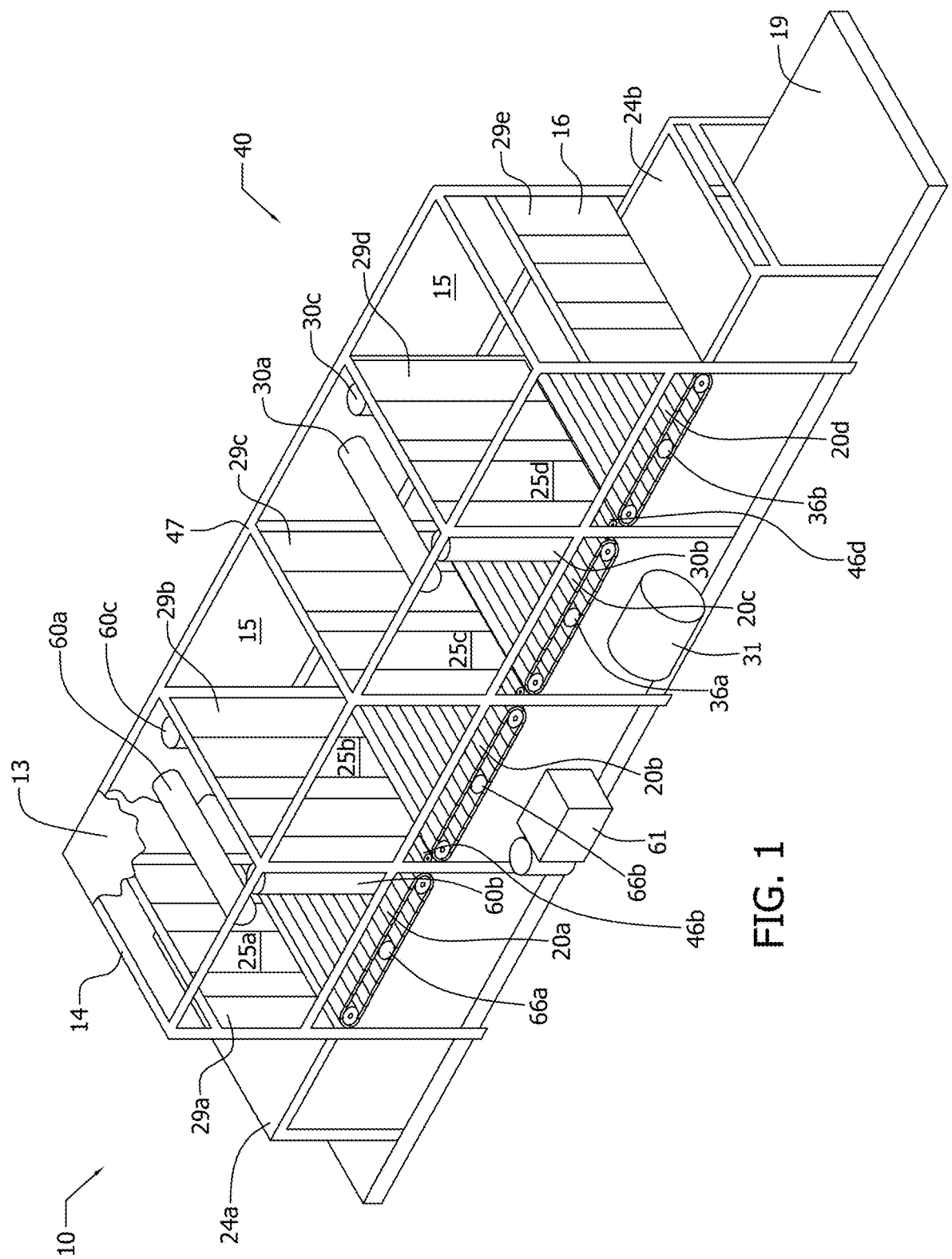
FIG. 1 illustrates by cut-away perspective view an exemplary implementation of a disinfection apparatus.

The Figures are exemplary only, and the implementations illustrated therein are selected to facilitate explanation. The number, position, relationship, and dimensions of the elements shown in the Figures to form the various implementations described herein, as well as dimensions and dimensional proportions to conform to specific force, weight, strength, flow and similar requirements are explained herein or are understandable to a person of ordinary skill in the art upon study of this disclosure. Where used in the various Figures, the same numerals designate the same or similar elements. Furthermore, when the terms "top," "bottom," "right," "left," "forward," "rear," "first," "second," "inside," "outside," and similar terms are used, the terms should be understood in reference to the orientation of the implementations shown in the drawings and are utilized to facilitate description thereof. Use herein of relative terms such as generally, about, approximately, essentially, may be indicative of engineering, manufacturing, or scientific tolerances such as ±0.1%, ±1%, ±2.5%, ±5%, or other such tolerances, as would be recognized by those of ordinary skill in the art upon study of this disclosure.

DETAILED DESCRIPTION OF THE INVENTION

A disinfection apparatus includes one or more conveyor belts that convey an object through a chamber, in various aspects. In various aspects, the disinfection apparatus includes a nozzle array comprising at least one nozzle positioned beneath the conveyor belt to spray a disinfectant through apertures formed in the conveyor belt onto at least portions of a surface of the object oriented toward the conveyor belt, the spray being communicated through apertures formed in the conveyor belt. The disinfection apparatus, in various aspects, includes a blower array comprising at least one blower nozzle positioned beneath the conveyor belt to blow an air jet through apertures formed in the conveyor belt onto at least portions of the surface of the object oriented toward the conveyor belt to dry the disinfectant from the object, the air jet being communicated through apertures formed in the conveyor belt. The disinfectant comprises water, and the disinfectant as sprayed from the nozzle array comprises droplets having droplet sizes within a range of from about 10 μm to about 100 μm, in various aspects. In various aspects, the object is repositioned with respect to apertures in the conveyor belt(s) as the object is conveyed through the chamber in order to allow spraying of disinfectant upon an entirety of the surface(s) of the object oriented toward the conveyor belt(s), and in order to allow blowing of air jet(s) upon an entirety of the surface(s) of the object oriented toward the conveyor belt(s).

FIG. 1 illustrates exemplary disinfection apparatus 10 including conveyor assembly 40 that includes conveyor belts 20a, 20b, 20c, 20d and conveyors 24a, 24b. Cover 13 is disposed over conveyor belts 20a, 20b, 20c, 20d in securement to portions of frame 47 to define chamber 15 over conveyor belts 20a, 20b, 20c, 20d. Only portions of cover 13 are included in the cut-away illustration of FIG. 1 for clarity. Cover 13 may be transparent, translucent, non-transparent, or combinations thereof, in various implementations. Cover 13 may be formed, for example, of a solid non-flexible material such as polycarbonate or methyl methacrylate, in some implementations, or cover 13 may be formed of a flexible material such as fabric or low-density polyethylene secured to portions of frame 47 to be stretched between portions of frame 47, in other implementations.

Conveyor 24a is in operable communication with conveyor belt 20a at end 14 of chamber 15 and conveyor 24b is in operable communication with conveyor belt 20d at end 16 of chamber 15, in this implementation. Curtain assemblies 29a, 29e are disposed at ends 14, 16 of chamber 15, respectively, and curtain assemblies 29b, 29c, 29d are disposed within chamber 15 to divide chamber 15 into sub-chambers 25a, 25b, 25c, 25d, as illustrated. Curtain assemblies 29a, 29b, 29c, 29d, 29e may be formed, for example, of strips of fabric, rubber, or low-density polyethylene, or configured in other ways to allow passage of object 99 therethrough as object 99 is conveyed through chamber 15 while otherwise enclosing sub-chambers 25a, 25b, 25c, 25d. Curtain assemblies 29a, 29b, 29c, 29d, 29e may be omitted in some implementations so that chamber 15 is not subdivided. In other implementations, any number of curtain assemblies may be included to subdivide chamber 15 into any number of sub-chambers. Spill platform 19 underlies conveyor assembly 40 including conveyor belts 20a, 20b, 20c, 20d and conveyors 24a, 24b to collect excess disinfectant 11, if any, that may fall from conveyor assembly 40.

Figure 2:
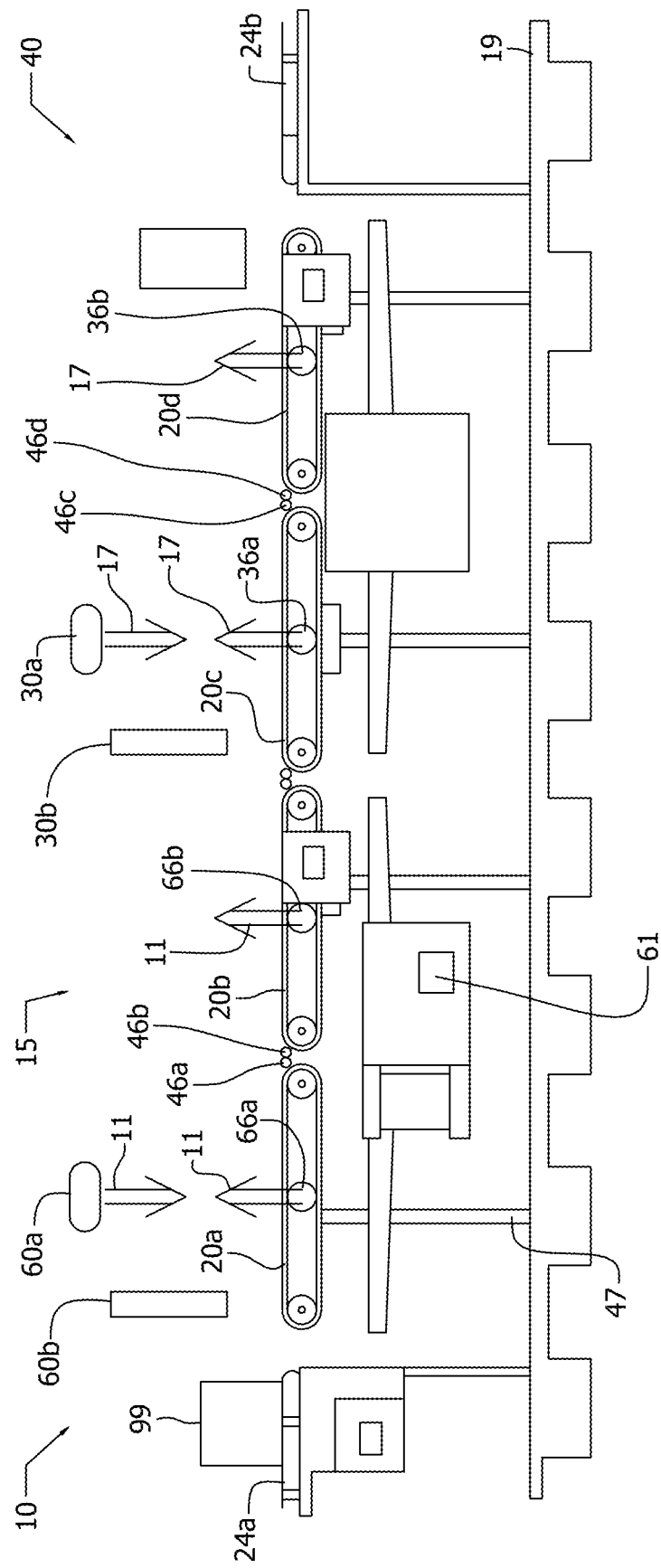
FIG. 2 illustrates by elevation view portions of the exemplary disinfection apparatus of FIG. 1.
Figure 4A:
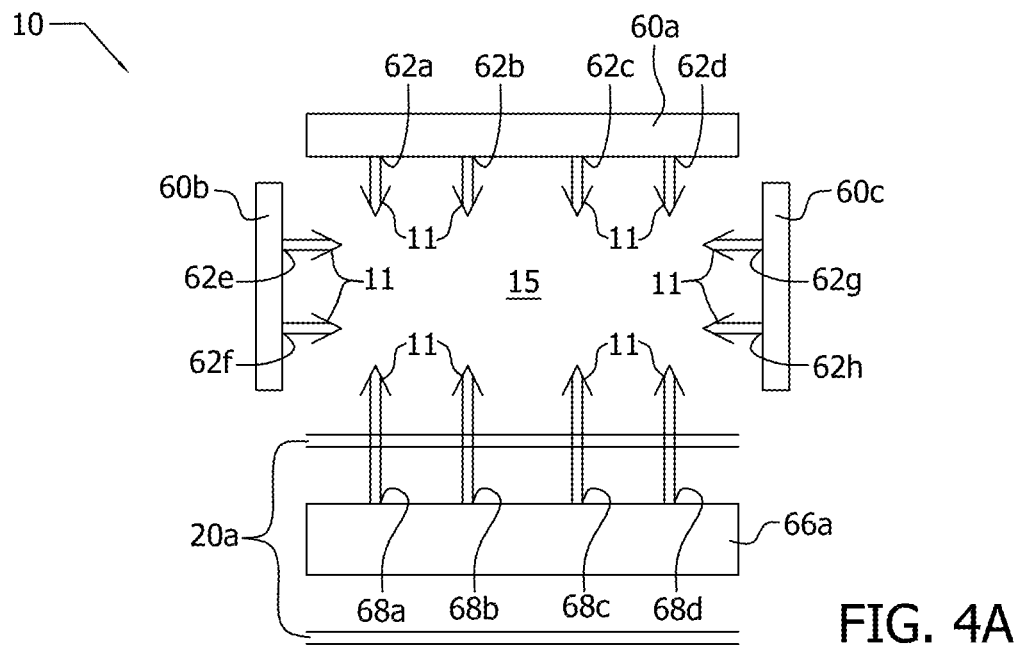
FIG. 4A illustrates by cross-sectional elevation view portions of the exemplary disinfection apparatus of FIG. 1.

As illustrated in FIGS. 1 and 2, nozzle arrays 60a, 60b, 60c are mounted within sub-chamber 25a of chamber 15 to spray disinfectant 11 onto surfaces 98a, 98b, 98c, 98d, 98e (see FIG. 5B) of object 99 as object 99 is conveyed through sub-chamber 25a by conveyor belt 20a. Nozzle arrays 60a, 60b, 60c include multiple nozzles 62a, 62b, 62c, 62d, 62e, 62f, 62g, 62h, as illustrated in FIG. 4A. As illustrated, nozzle arrays 60a, 60b, 60c are configured to spray disinfectant 11 onto surfaces 98a, 98b, 98c, 98d, 98e of object 99 other than surface 98f of object 99 that is oriented toward conveyor belt 20a as object 99 is conveyed through sub-chamber 25a. As illustrated in FIG. 4A, nozzle array 60a includes nozzles 62a, 62b, 62c, 62d disposed across conveyor belt 20a transverse to the motion of conveyor belt 20a and positioned above conveyor belt 20a to spray disinfectant 11 downward onto surfaces 98a, 98b, 98c, 98d, 98e of object 99 as object 99 is conveyed through sub-chamber 25a. Nozzle array 60b that includes nozzles 62e, 62f and nozzle array 60c that includes nozzles 62g, 62h are positioned at opposite sides of conveyor belt 20a to spray disinfectant 11 laterally onto surfaces 98a, 98b, 98c, 98d, 98e of object 99 as object 99 is conveyed through sub-chamber 25a, as illustrated in FIG. 4A.

As illustrated, nozzle arrays 66a, 66b are disposed beneath conveyor belts 20a, 20b, respectively, to spray disinfectant 11 through conveyor belts 20a, 20b onto surface 98f of object 99 that is oriented toward conveyor belts 20a, 20b as object 99 is conveyed through sub-chambers 25a, 25b. Nozzle array 66a, as illustrated in FIG. 4A, includes nozzles 68a, 68b, 68c, 68d disposed across conveyor belt 20a transverse to the motion of conveyor belt 20a. Nozzle array 66b may be configured similarly to nozzle array 66a. Various other implementations may have any number of nozzle arrays, such as nozzle arrays 60a, 60b, 60c, 66a, 66b, disposed within chamber 15, and the nozzle arrays may have any number of nozzles, such as nozzles 62a, 62b, 62c, 62d, 62e, 62f, 62g, 62h, 68a, 68b, 68c, 68d, with various orientations to spray disinfectant 11 onto surfaces 98a, 98b, 98c, 98d, 98e, 98f of object 99 as object 99 is conveyed through chamber 15.

Pump 61 fluidly communicates with nozzle arrays 60a, 60b, 60c, 66a, 66b to provide disinfectant 11 under pressure to nozzle arrays 60a, 60b, 60c, 66a, 66b to be sprayed by nozzles 62a, 62b, 62c, 62d, 62e, 62f, 62g, 62h, 68a, 68b, 68c, 68d of nozzle arrays 60a, 60b, 60c, 66a, 66b onto object 99, in this implementation. Pump 61 and nozzles of nozzle arrays 60a, 60b, 60c, 66a, 66b may be, for example, manufactured by Mistcooling, Inc of Brookshire Tex., and exemplary pump 61 from this manufacturer may pressurize disinfectant 11 to 1,500 psi. Accordingly, disinfectant 11 may be sprayed from nozzle arrays, such as nozzle arrays 60a, 60b, 60c, 66a, 66b, as a mist, fine droplets, or fog within sub-chambers 25a, 25b. Curtain assemblies 29a, 29b, 29c may contain, at least in part, disinfectant 11 within sub-chambers 25a, 25b, in this implementation. Disinfectant 11 as sprayed from nozzle arrays may have a droplet size of less than about 100 μm, in various implementations.

Disinfectant 11 may be liquid that may comprise water and may further comprise one or more substances effective to eliminate pathogens such as bacteria, viruses, fungi, or combinations thereof, as would be readily recognized by those of ordinary skill in the art upon study of this disclosure. In certain implementations, disinfectant 11 as sprayed from nozzle arrays 60a, 60b, 60c, 66a, 66b may have droplet sizes within a range of from about 10 μm to about 100 μm.

Disinfectant 11 may be pumped from a reservoir (not shown) or other supply by pump 61 to nozzle arrays 60a, 60b, 60c, 66a, 66b.

Figure 4B:
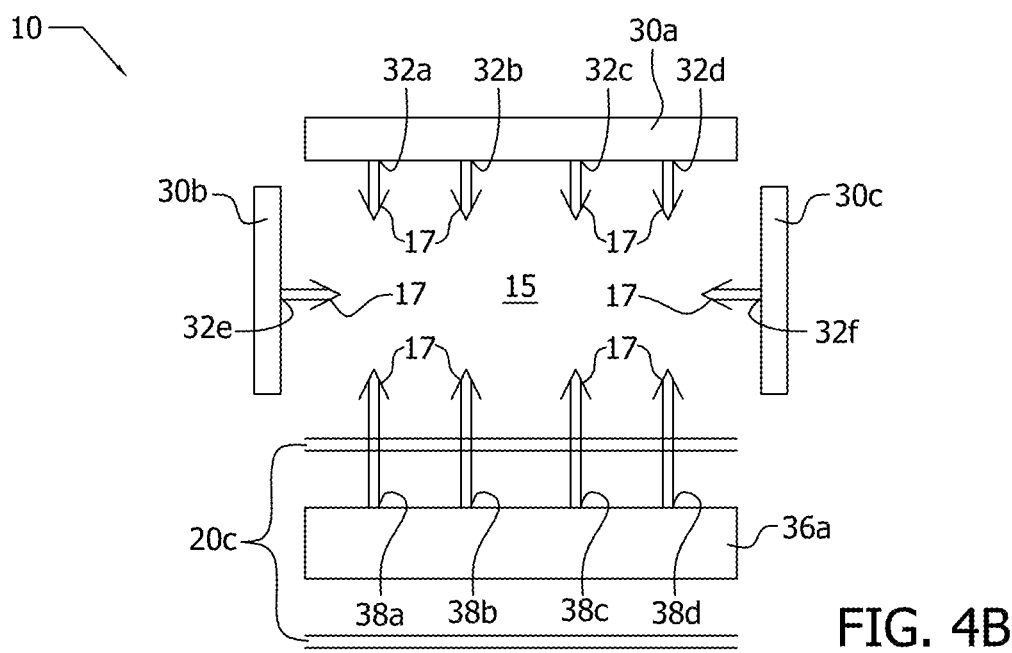
FIG. 4B illustrates by cross-sectional elevation view portions of the exemplary disinfection apparatus of FIG. 1.

As illustrated in FIGS. 1 and 2, blower array 30a is mounted above conveyor belt 20c within sub-chamber 25c and oriented horizontally to blow air jets 17 downward onto object 99, and blower arrays 30b, 30c are mounted on either side of conveyor belt 20c within sub-chamber 25c and oriented vertically to blow air jets 17 laterally onto object 99 to dry disinfectant 11 from object 99 as object 99 is conveyed through sub-chamber 25c by conveyor belt 20c. Blower arrays 30a, 30b, 30c are configured to dry disinfectant 11 from surfaces 98a, 98b, 98c, 98d, 98e of object 99 other than surface 98f of object 99 that is oriented toward conveyor belt 20c by blowing air jets 17 onto object 99 as object 99 is conveyed through sub-chamber 25c. As illustrated in FIG. 4B, blower array 30a includes multiple blower nozzles 32a, 32b, 32c, 32d, blower array 30b includes blower nozzle 32e, and blower array 30c includes blower nozzle 32f. Of course, any number of blower arrays, such as blower arrays 30a, 30b, 30c, each having any number of blower nozzles, such as blower nozzles 32a, 32b, 32c, 32d, 32e, 32f, may be positioned within sub-chamber 25c to blow any number of air jets 17 onto object 99 as object 99 is conveyed through sub-chamber 25c by conveyor belt 20c in order to dry disinfectant 11 from object 99.

As illustrated blower arrays 36a, 36b are disposed beneath conveyor belts 20c, 20d, respectively, to blow air jets 17 through conveyor belts 20c, 20d onto surface 98f of object 99 that is oriented toward conveyor belts 20c, 20d as object 99 is conveyed through sub-chambers 25c, 25d in order to dry disinfectant 11 from surface 98f of object 99 that is oriented toward conveyor belts 20c, 20d. Blower array 36a includes blower nozzles 38a, 38b, 38c, 38d disposed across conveyor belt 20c transverse to the motion of conveyor belt 20c, and blower array 36b may be configured similarly to blower array 36a. In other implementations, blower arrays, such as blower array 36a, 36b, may include any number of blower nozzles, such as blower nozzles 38a, 38b, 38c, 38d. Fan unit 31 communicates air from the ambient environment to blower arrays 30a, 30b, 30c, 36a, 36b that is then blown forth from blower nozzles 32a, 32b, 32c, 32d, 32e, 32f, 38a, 38b, 38c, 38d of blower arrays 30a, 30b, 30c, 36a, 36b as air jets 17, in this implementation. Fan unit 31 may be, for example, a model #A56CVF-8AC manufactured by Air Systems International. Curtain assemblies 29c, 29d, 29e may contain, at least in part, air jets 17 blown from blower arrays 30a, 30b, 30c, 36a, 36b within sub-chambers 25c, 25d, and curtain assemblies 29c, 29d, 29e may prevent dispersal of disinfectant 11 from sub-chambers 25c, 25d by air jets 17 as disinfectant 11 is dried from object 99 by blower arrays 30a, 30b, 30c, 36a, 36b.

As illustrated in FIG. 2, frame 47 includes various structural elements and so forth, as would be readily recognized by those of ordinary skill in the art upon study of this disclosure. Note that cover 13 is omitted from FIG. 2 for clarity of explanation. Conveyor belts 20a, 20b, 20c, 20d are mounted to frame 47 in looped powered rotation in various ways, as would be readily recognized by those of ordinary skill in the art upon study of this disclosure, and conveyor belts 20a, 20b, 20c, 20d cooperate mechanically with one another to convey object 99 into chamber 15, through chamber 15, and out of chamber 15, as illustrated.

It should be noted that the conveyors 24a, 24b are exemplary, and conveyors 24a, 24b encompass other material handling devices that may cooperate with ends 14, 16, respectively, of chamber 15. Conveyors 24a, 24b may be formed, for example, as a solid conveyor belt, rotatable wheels, rollers, walkway, and so forth, as would be readily recognized by those of ordinary skill in the art upon study of this disclosure. For example, conveyors 24a, 24b may be configured as ramps that cooperate with conveyor belts 20a, 20d to allow transfer of object 99 onto conveyor belt 20a and from conveyor belt 20d at ends 14, 16, respectively, of chamber 15. In certain implementations, object 99 may be transferred to and from conveyor belts 20a, 20d in various other ways than by conveyors 24a, 24b, so that conveyors 24a, 24b may be omitted in such implementations. For example, conveyor belts 20a, 20d at ends 14, 16, respectively, of chamber 15 may be configured to cooperate with a loading dock, platform, tailgate, trailer bed, truck bed, pallet on a forklift or pallet jack, packaging machine, or other material handling device or combination of material handling devices for transfer of object 99 onto conveyor belt 20a and transfer of object 99 from conveyor belt 20d.

Figure 5A:
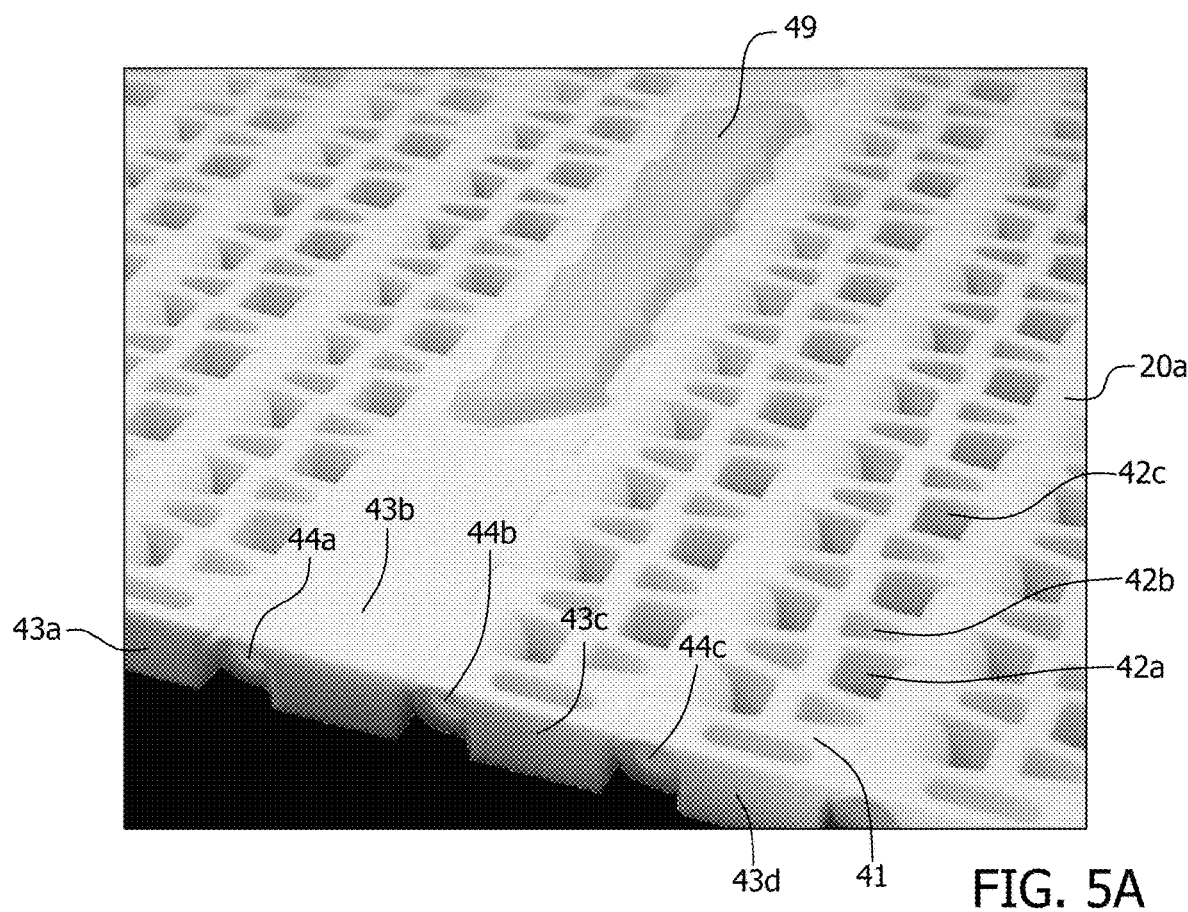
FIG. 5A illustrates by perspective view portions of the exemplary disinfection apparatus of FIG. 1.

As illustrated in FIG. 5A, conveyor belt 20a is comprised of sections, such as sections 43a, 43b, 43c, 43d, linked to one another by hinges, such as hinges 44a, 44b, 44c, that allow conveyor belt 20a to swivel including turning back on itself in order to be in looped rotation. Conveyor belt 20a may include gripping members, such as gripping member 49, that may assist in the engagement of conveyor belt 20a with object 99. For example, gripping member 49 may form a tractive surface with an increased coefficient of friction in comparison with a remainder of conveyor belt 20a to enhance frictional engagement of object 99 with conveyor belt 20a. In other implementations gripping member 49 may be formed as a hook, a slot, or suchlike configured to engage a particular object 99.

In this implementation, conveyor belts 20b, 20c, 20d are formed generally as conveyor belt 20a illustrated in FIG. 5A. In this implementation, every section, such as section 43a, 43b, 43c, 43d, of the conveyor belt, such as conveyor belt 20a, 20b, 20c, 20d, is formed of a structural member, such as structural member 41 of section 43d, as illustrated in FIG. 5A. As illustrated in FIG. 5A, apertures are formed in the structural members, such as apertures 42a, 42b, 42c formed in structural member 41, that pass through the structural members to allow passage of disinfectant 11 or air jets 17 through the structural members of the conveyor belt to contact portions of surface 98f of object 99 oriented toward apertures. For example, as illustrated in FIG. 4A, disinfectant 11 from nozzle array 66a is sprayed through conveyor belt 20a by being sprayed through apertures, such as apertures 42a, 42b, 42c, formed in conveyor belt 20a to contact surface 98f of object 99. As illustrated in FIG. 4B, for example, air jets 17 from blower array 36a is blown through conveyor belt 20c by being blown through apertures, such as apertures 42a, 42b, 42c, formed in conveyor belt 20c to contact surface 98f of object 99.

Figure 3A:
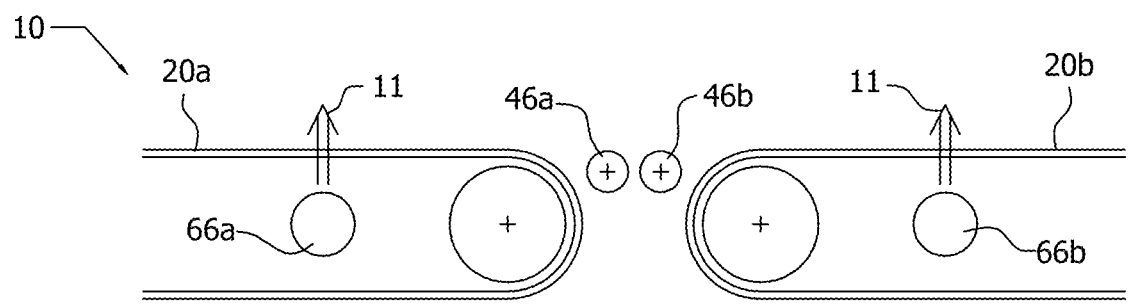
FIG. 3A illustrates by elevation view portions of the exemplary disinfection apparatus of FIG. 1.
Figure 3B:
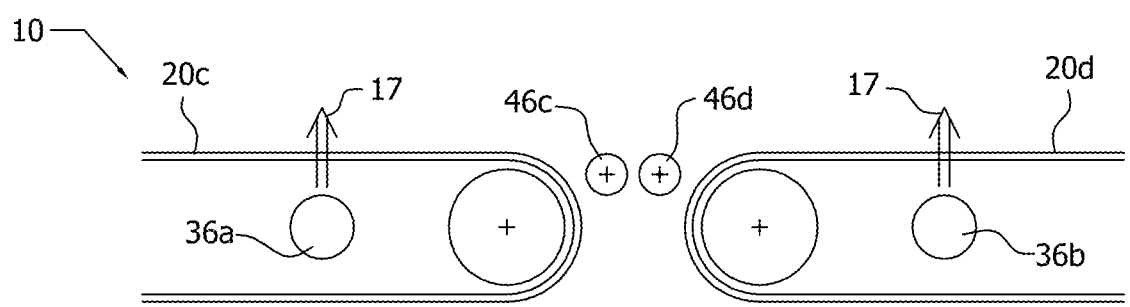
FIG. 3B illustrates by elevation view portions of the exemplary disinfection apparatus of FIG. 1.

FIG. 3A illustrates portions of conveyor belt 20a and conveyor belt 20b with conveyor belt 20a in mechanical cooperation with conveyor belt 20b, and FIG. 3B illustrates portions of conveyor belt 20c and conveyor belt 20d with conveyor belt 20c in mechanical cooperation with conveyor belt 20d. The structural members, such as structural member 41, of conveyor belts 20a, 20b occlude portions of surface 98f of object 99 from being sprayed with disinfectant 11, and the structural members of conveyor belts 20c, 20d occlude portions of surface 98f of object 99 from being blown by air jets 17 through the conveyor belt. In exemplary disinfection apparatus 10, surface 98f of object 99 is repositioned with respect to the structural members and the apertures passing through the structural members to spray disinfectant 11 and blow air jets 17 onto an entirety of surface 98f.

For example, as illustrated in FIG. 3A, rollers 46a, 46b are rotatably positioned between conveyor belts 20a, 20b, and object 99 is transferred from conveyor belt 20a onto conveyor belt 20b by passing across rollers 46a, 46b. The transfer of object 99 across rollers 46a, 46b repositions surface 98f of object 99 with respect to apertures and structural members of conveyor belts 20a, 20b. For example, after transfer across rollers 46a, 46b from conveyor belt 20a to conveyor belt 20b, portions of surface 98f of object 99 occluded by structural members of conveyor belt 20a may be in communication with apertures of conveyor belt 20b to allow spraying thereof with disinfectant 11 from nozzle array 66b. Thus, differing portions of surface 98f are occluded by structural members of conveyor belt 20a, 20b so that portions of surface 98f of object 99 occluded by structural members of conveyor belt 20a are sprayed with disinfectant 11 through apertures in conveyor belt 20b by nozzle array 66b and vice versa. For example, by repositioning surface 98f of object 99 with respect to structural members and apertures, all portions of surface 98f of object 99 are in fluid communication with apertures in conveyor belt 20a, apertures in conveyor belt 20b, or both apertures in conveyor belt 20a and apertures in conveyor belt 20b so that disinfectant 11 may be sprayed upon an entirety of surface 98f of object 99 by nozzle array 66a and by nozzle array 66b.

While exemplary disinfection apparatus 10 is illustrated as having two conveyor belts 20a, 20b with two nozzle arrays 66a, 66b disposed underneath, it should be recognized that other implementations may utilize any number of conveyor belts and nozzle arrays with corresponding multiple repositioning of object 99 with respect to structural members and apertures in order to ensure that disinfectant 11 is sprayed upon the entirety of surface 98f of object 99.

As illustrated in FIG. 3B, rollers 46c, 46d are rotatably positioned between conveyor belts 20c, 20d, and object 99 is transferred from conveyor belt 20c onto conveyor belt 20d across rollers 46c, 46d. The transfer of object 99 across rollers 46c, 46d repositions surface 98f of object 99 with respect to apertures and structural members of conveyor belts 20c, 20d. For example, after transfer across rollers 46c, 46d from conveyor belt 20c to conveyor belt 20d, portions of surface 98f of object 99 occluded by structural members of conveyor belt 20c may be in fluid communication with apertures of conveyor belt 20d so that blower array 36b may blow air jet 17 onto these surfaces of object 99. Thus, different portions of surface 98f of object 99 are occluded by structural members of conveyor belt 20c, 20d so that air jet 17 from blower array 36b contacts portions of surface 98f of object 99 occluded by structural members of conveyor belt 20c and air jet 17 from blower array 36a contacts portions of surface 98f of object 99 occluded by structural members of conveyor belt 20d. Thus, by reorienting surface 98f of object 99 with respect to structural members and apertures of conveyor belts 20c, 20d, disinfectant 11 is dried from an entirety of surface 98f of object 99 by air jet 17 from blower array 36a and air jet 17 from blower array 36b, for example. Again, while exemplary disinfection apparatus 10 is illustrated as having two conveyor belts 20c, 20d with two blower arrays 36a, 36b disposed underneath to dry disinfectant 11 from surface 98f of object 99 that is oriented toward the conveyor belts 20c, 20d, it should be recognized that other implementations may utilize any number of conveyor belts and blower arrays in order to ensure that disinfectant 11 is dried from surface 98f of object 99.

Figure 5B:
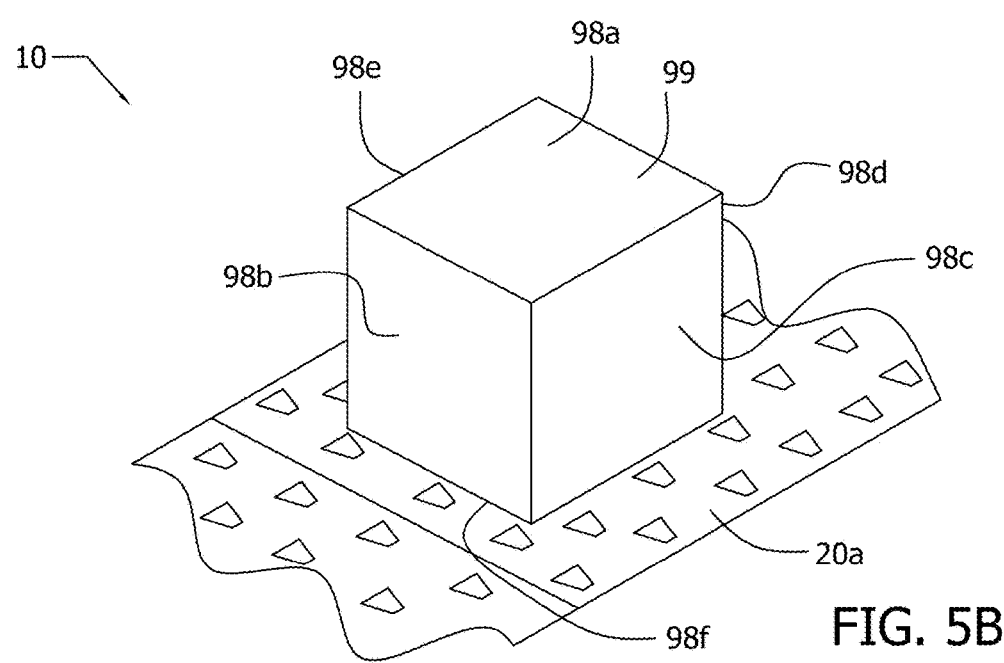
FIG. 5B illustrates by perspective view portions of the exemplary disinfection apparatus of FIG. 1 including an exemplary object; and, FIG. 6 illustrates by cut-away perspective view portions of another exemplary implementation of a disinfection apparatus.

Object 99 is illustrated as a cube with surfaces 98a, 98b, 98c, 98d, 98e, 98f in FIG. 5B for explanatory purposes. It should be recognized that object 99 may have any geometric configuration with any number of surfaces with one or more surfaces oriented toward the conveyor belts, as per surface 98f, and other surfaces oriented away from the conveyor belts, as per surfaces 98a, 98b, 98c, 98d, 98e. Any number of objects, such as object 99, may be conveyed through chamber 15 simultaneously, and the objects may have a variety of geometric configurations, in various implementations.

Figure 6:
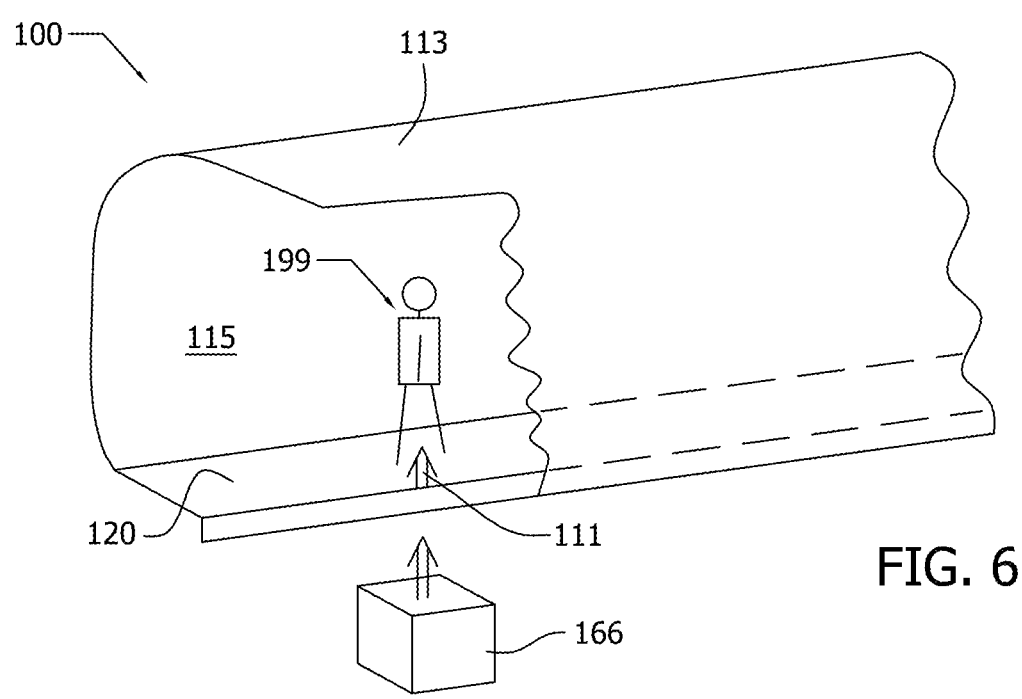

FIG. 6 illustrates exemplary disinfection apparatus 100 adapted to disinfect object 199 configured as a person. As illustrated in FIG. 6, disinfectant 111 is sprayed from nozzle array 166 through conveyor belt 120 onto object 199 positioned on conveyor belt 120. Conveyor belt 120 includes apertures, such as apertures 42a, 42b, 42c, for fluid communication of disinfectant 111 through conveyor belt 120 onto object 199. Cover 113 forms chamber 115 having a tunnel like configuration that encloses conveyor belt 120 including object 199 and cover 113 is sized to accommodate object 199. A number of nozzle arrays, such as nozzle arrays 60a, 60b, 60c, 66a, 66b, 166, may be positioned in fluid communication with chamber 115 to spray disinfectant 111 onto object 199 as object 199 is conveyed through chamber 115. A number of blower arrays, such as blower array 30a, 30b, 30c, 36a, 36b, may be positioned in fluid communication with chamber 115 to blow an air jet, such as air jet 17, onto object 199 in order to dry disinfectant 111 from object 199 as object 199 is conveyed through chamber 115. Any number of conveyor belts, such as conveyor belt 120, 20a, 20b, 20c, 20d, may cooperate mechanically in order to convey object 199 through chamber 115.

Although generally omitted from the Figures for clarity of explanation, it should be understood that exemplary disinfection apparatus 10, 100 may include various electrical communication pathways for the communication of electrical power, digital signals, analogue signals, fluid communication pathways, and various controls, sensors (e.g. temperature), lights, ventilation (active or passive), wireless communication pathways, microcontrollers, and so forth, as would be readily recognized by those of ordinary skill in the art upon study of this disclosure.

In operation of an exemplary disinfection apparatus, such as disinfection apparatus 10, 100, an object, such as object 99, 199, may be placed upon a conveyor, such as conveyor 24a. The conveyor then conveys the object through an end of a chamber, such as end 14 of chamber 15, onto one or more conveyor belts, such as conveyor belt 20a, 20b, 20c, 20d, 120, that cooperate mechanically with one another to convey the object through the chamber. As the object is conveyed through the chamber, disinfectant, such as disinfectant 11, 111, is sprayed upon exposed surfaces of the object, such as surfaces 98a, 98b, 98c, 98d, 98e, by one or more nozzle arrays, such as nozzle arrays 60a, 60b, 60c, disposed above the conveyor belt(s). A nozzle array, such as nozzle arrays 66a, 66b, 166, disposed below conveyor belt(s) sprays the disinfectant upon surfaces of the object oriented toward the conveyor belt(s), such as surface 98f, by spraying the disinfectant through apertures, such as apertures 42a, 42b, 42c, formed within the conveyor belt(s) as the object is conveyed through the chamber.

As the object is conveyed through the chamber, air jets, such as air jet 17, are blown upon the exposed surfaces of the object by one or more blower arrays, such as blower arrays 30a, 30b, 30c, disposed above the conveyor belt(s). A blower array, such as blower arrays 36a, 36b, disposed below the conveyor belt(s) blows air jets through apertures upon surfaces of the object oriented toward the conveyor belt(s) as the object is conveyed through the chamber.

In implementations having multiple conveyor belts, surfaces of the object oriented toward the conveyor belts may be repositioned with respect to apertures and structural members, such as structural member 41, of the conveyor belts as the object is conveyed through the chamber. For example, the object may be transferred between conveyor belts across rollers, such as rollers 46a, 46b, 46c, 46d, thereby repositioning surfaces of the object with respect to apertures and structural members. For example, after transferring the object from a first conveyor belt to a second conveyor belt, surfaces of the object occluded by structural members of the first conveyor belt may be in fluid communication with apertures of the second conveyor belt and vice versa. Because, per this example, surfaces of the object occluded by structural members of the first conveyor belt are in fluid communication with apertures of the second conveyor belt, nozzle arrays disposed beneath the first conveyor belt and the second conveyor belt spray disinfectant onto an entirety of the surfaces of the object faced toward the conveyor belts. Again, per this example, because surfaces of the object occluded by structural members of the first conveyor belt are in fluid communication with apertures of the second conveyor belt, blower arrays disposed beneath the first conveyor belt and the second conveyor belt blow air jets onto an entirety of the surfaces of the object faced toward the conveyor belts.

After passing through the chamber, the object may then be transferred from the chamber onto a conveyor, such as conveyor 24b, through an end, such as end 16, of the chamber. At this stage of operation, surfaces of the object have been disinfected by spraying of the disinfectant thereupon by the nozzle arrays, and the disinfectant has been dried from the object by air jets blown onto the object by the blower arrays. The object, which is now disinfected by the disinfectant, may then be removed from the conveyor.

A spill platform, such as spill platform 19, disposed under a conveyor assembly, such as conveyor assembly 40, collects disinfectant in liquid form that may fall from the conveyor assembly, in some implementations. Curtain assemblies, such as curtain assemblies 29a, 29b, 29c, 29d, 29e, may divide the chamber into sub-chambers, such as sub-chambers 25a, 25b, 25c, 25d, in some implementations. The curtain assemblies may be operable to allow passage of the object therethrough while generally enclosing the sub-chambers, for example, to contain the disinfectant or the air jet within the sub-chambers.

In implementations wherein the object is configured as a person, the person may walk into and out of the chamber, and the person may walk upon the conveyor belt(s) within the chamber to be variously positioned with respect to the apertures in the conveyor belt(s) while being conveyed through the chamber by the conveyor belt(s) in order that disinfectant may be sprayed through the apertures onto an entirety of surfaces of the person including surfaces of the person oriented toward the conveyor belt(s) and in order that air jets may be blown through the apertures onto an entirety of surfaces of the person including surfaces of the person oriented toward the conveyor belt(s). The person may transfer between conveyor belts under their own motility to be variously positioned with respect to the apertures in order to spray disinfectant through the apertures onto an entirety of surfaces of the person oriented toward the conveyor belts and to blow air jets through the apertures onto an entirety of surfaces of the person oriented toward the conveyor belts. Movement of the person with respect to the apertures in the conveyor belt(s) by walking, transfer between conveyor belts, or walking and transfer between conveyor belts may allow spraying of disinfectant through the apertures onto an entirety of surfaces of the person oriented toward the conveyor belt(s) and may allow blowing of air jets through the apertures onto an entirety of surfaces of the person oriented toward the conveyor belt(s).

The foregoing discussion along with the Figures discloses and describes various exemplary implementations. These implementations are not meant to limit the scope of coverage, but, instead, to assist in understanding the context of the language used in this specification and in the claims. The Abstract is presented to meet requirements of 37 C.F.R. § 1.72(b) only. Accordingly, the Abstract is not intended to identify key elements of the apparatus and methods disclosed herein or to delineate the scope thereof. Upon study of this disclosure and the exemplary implementations herein, one of ordinary skill in the art may readily recognize that various changes, modifications, and variations can be made thereto without departing from the spirit and scope of the inventions as defined in the following claims.

The invention claimed is:

1. A method of disinfecting an object, comprising the steps of:
   a) providing a disinfection apparatus, comprising:
      i) a chamber having a disinfecting zone and a drying zone;
      ii) a plurality of conveyors that cooperate with one another to convey the object through the chamber, the plurality of conveyors including a disinfecting conveyor located in the disinfecting zone and a drying conveyor located in the drying zone, the disinfecting conveyor having a first disinfecting conveyor belt having apertures therethrough and a second disinfecting conveyor belt having apertures therethrough, the drying conveyor having a first drying conveyor belt having apertures therethrough and a second drying conveyor belt having apertures therethrough;
      iii) an upper disinfecting device located in the disinfecting zone above the disinfecting conveyor for spraying a disinfectant onto the object as the object is conveyed through the disinfecting zone;
      iv) a first lower disinfecting device located in the disinfecting zone below the first disinfecting conveyor belt for spraying a disinfectant through the apertures in the first disinfecting conveyor belt and onto portions of a lower surface of the object that are aligned with the apertures through the first disinfecting conveyor belt as the object is conveyed through the disinfecting zone;
      v) a second lower disinfecting device located in the disinfecting zone below the second disinfecting conveyor belt for spraying a disinfectant through the apertures in the second disinfecting conveyor belt and onto portions of the lower surface of the object that are aligned with the apertures through the second disinfecting conveyor belt as the object is conveyed through the disinfecting zone;
      vi) an upper blowing device located in the drying zone above the drying conveyor for blowing air onto the object as it is conveyed through the drying zone;
      vii) a first lower blowing device located in the drying zone below the first drying conveyor belt for blowing air through the apertures in the first drying conveyor belt and against portions of the lower surface of the object that are aligned with the apertures through the first drying conveyor belt as the object is conveyed through the drying zone; and viii) a second lower blowing device located in the drying zone below the second drying conveyor belt for blowing air through the apertures in the second drying conveyor belt and against portions of the lower surface of the object that are aligned with the apertures through the second drying conveyor belt as the object is conveyed through the drying zone;

b) conveying the object through the disinfecting zone, wherein the object is sprayed with disinfectant from the upper disinfecting device, the first lower disinfecting device, and the second lower disinfecting device as the object is conveyed through the disinfecting zone;

c) transferring the object from the first disinfecting conveyor belt to the second disinfecting conveyor belt as the object is conveyed through the disinfecting zone, wherein the lower surface of the object is repositioned to promote disinfection of the entire lower surface of the object as the object is transferred from the first disinfecting conveyor belt to the second disinfecting conveyor belt;

d) conveying the object through the drying zone, wherein the object is dried with air blown from the upper blowing device, the first lower blowing device, and the second lower blowing device as the object is conveyed through the drying zone; and e) transferring the object from the first drying conveyor belt to the second drying conveyor belt as the object is conveyed through the drying zone, wherein the lower surface of the object is repositioned to promote drying of the entire lower surface of the object as the object is transferred from the first drying conveyor belt to the second drying conveyor belt.

2. A method according to claim 1, wherein the disinfection apparatus further comprises one or more rollers located between the first disinfecting conveyor belt and the second disinfecting conveyor belt to promote repositioning of the object as the object is transferred from the first disinfecting conveyor belt, over the one or more rollers, and to the second disinfecting conveyor belt.

3. A method according to claim 1, wherein the disinfection apparatus further comprises one or more rollers located between the first drying conveyor belt and the second drying conveyor belt to promote repositioning of the object as the object is transferred from the first drying conveyor belt, over the one or more rollers, and to the second drying conveyor belt.

* * * * *